United States Patent [19]

Messina et al.

[11] 4,216,345
[45] Aug. 5, 1980

[54] PREPARATION OF LINEAR ALKYLBENZENES

[75] Inventors: Giuseppe Messina, Alghero; Loreno Lorenzoni, Porto Torres; Lucio Di Fiore, Milan, all of Italy

[73] Assignee: Euteco S.p.A., Milan, Italy

[21] Appl. No.: 946,929

[22] Filed: Sep. 28, 1978

[51] Int. Cl.² .......................... C07C 15/02; C07C 7/13
[52] U.S. Cl. .................................. 585/323; 585/455; 585/826; 585/935
[58] Field of Search ................. 260/671 B, 671 R; 585/323, 455, 823, 935

[56] References Cited

U.S. PATENT DOCUMENTS

| 3,053,913 | 9/1962 | Norris | 260/671 B |
| 3,383,430 | 5/1968 | Hutson, Jr. et al. | 260/671 B |
| 3,426,086 | 2/1969 | Gray et al. | 260/671 B |
| 3,931,350 | 1/1976 | Sparks | 260/671 B |

*Primary Examiner*—George Crasanakis
*Attorney, Agent, or Firm*—Sughrue, Rothwell, Mion, Zinn and Macpeak

[57] ABSTRACT

Process for the preparation of alkylbenzenes by partial chlorination of linear $C_9$–$C_{15}$ paraffins, catalytic alkylation of benzene with the resulting mixture and fractionation by distillation of the alkylation products.

At least a part of the unreacted paraffins recovered by fractionation and to be recycled to the chlorination stage is submitted, continuously or intermittently, to a purification treatment with molecular sieves.

The content in undesired by-products of the alkylbenzenes can thus be maintained at negligibly low values.

12 Claims, No Drawings

PREPARATION OF LINEAR ALKYLBENZENES

The present invention relates to improvements in the preparation of linear alkylbenzenes in which the alkyl radical consists of a linear chain containing from 9 to 15 atoms of carbon. Such products, as is known, are of great importance in the preparation of biologically-degradable detergents.

Alkylbenzenes having alkyl substituents consisting of a linear paraffin chain are normally prepared, on an industrial scale, by means of chlorination of the linear paraffins, alkylation of benzene, in the presence of Friedel Crafts catalysts, with the chlorinated paraffins thus obtained, and fractionation of the alkylated product, after separation of the catalyst, into the component members of the product by means of distillation.

In such processes, in order to obtain the maximum yield of monochloroparaffins, the chlorination stage is carried out with a high paraffin/chlorine molar ratio. As a result, part of the paraffins does not react.

The mixture of chlorinated paraffins and unreacted paraffins thus obtained, given the difficulties of separation, is conveyed directly to the alkylation stage. The unreacted paraffins are subsequently recovered by distillation of the alkylation products and recycled to the chlorination stage.

In the processes under discussion, there is a gradual accumulation of by-products, both in the recycled paraffins and in the alkylbenzenes produced.

In particular, the accumulation of chlorinated products in the alkylbenzenes is such that the chlorine content may reach undesirable values; moreover, due to the presence of aromatic by-products, the alkylbenzenes often give disagreeable odours.

Similarly, with regard to the impurities accumulating in the recycled paraffins, the most harmful and consistent are due to chlorinated and unchlorinated aromatic by-products. These impurities, when they are recycled together with the paraffins, may undergo further modifications in the chlorination and akylation stages, with formation of heavier products which separate in the subsequent distillation stage with the alkylbenzenes.

In each case, the alkylbenzenes obtained are rich in impurities, especially chlorinated products, which often give disagreable odours and have other undesirable characteristics, especially corrosive and toxic properties. All this creates problems which are difficult to solve, given that it is necessary for the alkylbenzenes used in commercial detergent formulations to be practically totally free of chlorine and disagreeable odours.

A process for the production of linear alkylbenzenes by alkylation of benzene with chlorinated paraffins, by means of which it is possible to avoid the disadvantages described above, has already formed the subject of Italian patent specification No. 839,022. In particular, by means of this process, it is possible to obtain linear alkylbenzenes with an extremely low content of by-products, especially chlorinated products, and free from undesirable odours.

More precisely, according to this process, the recycled products, consisting essentially of paraffins, are subjected to a hot treatment with sulphuric acid, oleum or sulphur trioxide, and the product obtained is decanted, after cooling, so as to separate the acidic sludges. The paraffins finally isolated are recycled to the chlorination stage. This process allows high quality, linear alkylbenzenes to be obtained directly without the necessity of further treatments of the alkylbenzenes. It should be noted in this connection that, to obtain high quality, linear alkylbenzenes directly in a continuous process, it is not sufficient to use pure, or practically pure, fresh paraffins but it is essential to subject the recycled paraffins to the treatment described above. This process, however, results in a loss, if only less than 0.5% of the paraffins which are subjected to the acid treatment and requires, moreover, a series of operative stages.

We have now found that it is possible to obtain, in a more economic way, and with a simpler method of operation, linear alkylbenzenes having still further improved characteristics without substantial loss of product.

Thus, the invention provides a process for the preparation of alkylbenzenes by partial chlorination of linear paraffins having from 9 to 15 carbon atoms per molecule, catalytic alkylation of benzene using the resulting mixture of chlorinated and unreacted paraffins, fractionation by distillation, after separation of the catalyst, of the alkylation products thus obtained and recycling of the unreacted paraffins recovered from the fractionation stage to the partial chlorination stage, characterized in that at least a part of the unreacted paraffins to be recycled to the partial chlorination stage is submitted, continuously or intermittently, to a purification treatment with molecular sieves.

This treatment may be carried out, in a continuous or a discontinuous manner, on the whole of the recycled paraffins or only on part of these, so as to eliminate the impurities either substantially completely or so as to keep them below the critical limits.

In every case, by means of the process of the present invention, it is possible to obtain linear alkylbenzenes of high quality, free from disagreeable odours, with a chlorine content less than 100 ppm and with a content of other impurities normally present, in particular aromatic by-products, which is substantially irrelevant.

In practice, the recycled paraffins, rich in impurities, are passed through one or more beds of molecular sieves. Generally fixed beds are used. Molecular sieves based on zeolites have been shown to be particularly useful. These are known commercially, for example, as molecular sieves of the type X and of the type Y, provided, for example, by the Union Carbide Corporation Linde Division and have pore sizes varying between about 9 and 10 Angstrom.

The molecular sieves of the type X have the composition

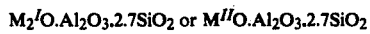

$$M_2^I O.Al_2O_3.2.7SiO_2 \text{ or } M^{II}O.Al_2O_3.2.7SiO_2$$

where M may be:
Na+(sieves type 13 X), Ca++(sieves 10 X), K+, Mg++, Ba++, NH4+or in general, an alkali or alkaline earth metal.

Nevertheless molecular sieves of the type X in which the alkali metal cation is substituted by other metals such as Ag+, Cu++, Co++ or metals of the rare earth group may also be used with profit. In the molecular sieves of the type X the Si/Al atomic ratio has a value close to 1.

The molecular sieves of the type Y are, however, much more rich in silica. The Si/Al atomic ratio is generally from 1.5 to 3.

A typical composition of a molecular sieve of the type Y is in fact the following (where the percentages are by weight):

$Na_2O$—13.5%, $Al_2O_3$—21.3%, $SiO_2$—65.2%.

The shapes and dimensions of the molecular sieves used are not a critical factor. The aforesaid adsorbents X and Y may hence be used in the form of powders, of small spheres or of cylindrical extrusions of variable sizes, such as are available commercially.

It has also been ascertained that the average absorbent capacity of the molecular sieves used, expressed in grams absorbed per grams of absorbent, varies from 8% to 15% for the aromatic by-products and the other types of secondary impurities present in the paraffins.

The temperature at which the passage of the paraffins through the bed of molecular sieves is carried out may be chosen within a relatively wide range. The best results have been obtained by operation at temperatures of from ambient temperature to 200° C. The operating pressure is preferably from 1 to 10 atmospheres.

The average residence time of the paraffins on the molecular sieves is generally from 5 minutes to 60 minutes.

Of particular importance is the fact that, by operating according to the manner described above, practically complete purification of the recycled paraffins may be obtained and the residual contents of chlorinated and unchlorinated aromatic compounds and of all the other secondary impurities contained therein may be reduced to levels lower than those detectable by flame gas-chromatography.

It should also be noted that, differing from several known methods for the purification of recycled paraffins, the method of the invention does not present problems of mixing and pollution of the said paraffins with chemical agents which must then be removed, nor problems of corrosion of the plant or pollution of the environment by discharge of harmful by-products.

Moreover, the efficiency of the purification is practically constant whatever the initial concentration of the impurities in the paraffins.

In practice, as already indicated, the purification treatment is carried out by passing the flow of paraffins to be purified over one or more fixed or moving beds of molecular sieves which, once exausted, may conveniently be regenerated by means of thermal stripping or of displacement by elution of the adsorbed substance. A pre-treatment of stripping with inert gas is generally carried out before the regeneration treatment, to recover the unreacted paraffins retained in the molecular sieves.

In the more frequent case in which it is desired to carry out the purifications continuously, it is evident that the installation of at least two absorption columns or devices which work alternately is necessary.

The purification treatment may be carried out as follows:

(a) passage of the paraffins through the absorbent until the latter is exhausted, which will be indicated by the reappearance of the immpurities in the paraffins which leave the absorption apparatus; and deviation of the paraffin flow to be purified towards new, "fresh" molecular sieves;

(b) stripping with inert gas at a temperature of from ambient temperature to 150° C., and at a pressure of from 1 to 10 atmospheres, of the paraffins retained mechanically between the particles of the exhausted absorbent;

(c) periodical regeneration of the exhausted molecular sieves.

Th purified paraffins leaving the absorption apparatus are recycled directly to the chlorination reactor. The chlorination mixture is hence fed directly to the alkylation stage to give the linear alkylbenzenes.

With regard to the regeneration mentioned at point (c), it is possible to use, with particular advantage, the three procedures which will be described hereinafter. All the three operating methods give extremely satisfactory and practically equivalent results although each one of these precedures offers decided, specific advantages.

(1) First method:

a stripping treatment for the molecular sieves at a temperature of from 250° to 400° C. and at pressures of from 1 to 10 atmospheres by means of an inert gas.

(2) Second method:

an elution treatment with a light aromatic hydrocarbon solvent, such as, for example, benzene, toluene, chlorobenzene, ethylbenzene or the like. The preferred eluent is benzene.

It has been found that the most suitable temperatures for the elution treatment are from ambient temperature to the boiling point of the eluent at the working pressure. The latter is advantageously maintained at a value of from 1 to 10 atmospheres.

The treatment of the molecular sieves by elution is generally followed by a stripping treatment of the eluent with an inert gas. This stage is carried out advantageously at a temperature of from 150° C. to 250° C., and preferably from 170° C. to 200° C. and at a pressure of from 1 to 10 atmospheres.

(3) Third method:

an elution treatment carried out under the conditions described above at point (2). This elution is followed by the direct resumption of the absorption cycle of the recycled impure paraffins on the molecular sieves, carried out under the usual operation conditions.

In this manner the impurities (aromatic by-products, etc.) contained in the paraffins displace the eluent from the molecular sieves to be absorbed in their turn. Obviously the first paraffin fraction leaving the absorption apparatus will contain a certain quantity of eluent which may easily be removed by means of conventional methods, preferably by means of distillation.

As already stated above, all the three systems described result in effective regeneration of the molecular sieves, which recover their absorbent capacity practically completely both in a quantitative and a qualitative sense. The choice of one or the other of the regeneration systems hence depends from time to time only on incidental criteria, in particular economic convenience, due, for example, to the availability or lack of availability of the chemical reagents, of the heating means, apparatus, etc.

With regard to the other steps of the process, these are carried out in a conventional manner. In a preferred embodiment:

(a) the chlorination of the linear $C_9$–$C_{15}$ paraffins (recycled and unrecycled) is carried out by operating with gaseous chlorine with a paraffin/chlorine molar ratio of from 2:1 to 10:1 and at a temperature of from 50° to 200° C. The mixture of products from the chlorination (chlorinated and unchlorinated paraffins), after degassing to remove the hydrogen chloride, is conveyed directly to the alkylation stage.

(b) the alkylation of benzene is carried out with the benzene in excess over the chlorinated paraffin, in the presence of $AlCl_3$, at a temperature of from 40° to 100° C. and for a period of from 30 minutes to 3 hours.

(c) the alkylation products, after decanting to separate the catalytic sludge and washing with aqueous alkali up to neutrality, are fractionated by distillation. Greater details will be given in Example 1.

EXAMPLE 1

Into a tubular reactor there are fed about 230 Kg/hour of gaseous chlorine and 1,650 Kg/hour of linear $C_9$–$C_{15}$ paraffins consisting of 70% by weight of recycled paraffins and for the remaining 30% of fresh, commercial paraffins.

The composition in percentage by weight of the n-paraffins, determined by gas-chromatographic analysis, is the following:

| | | | |
|---|---|---|---|
| $C_9$ | = trace % | $C_{10}$ | = 11.1% |
| $C_{11}$ | = 32% | $C_{12}$ | = 32.1% |
| $C_{13}$ | = 22.4% | $C_{14}$ | = 2.4% |
| $C_{15}$ | = 0.02% | | |

The chlorination of the paraffins is carried out at a temperature of about 110° C.

The products of chlorination, freed from the hydrogen chloride by degassing, are then fed to the alkylation stage, together with 250 Kg/hour of catalytic sludge. This latter consists of the exhausted sludge discharged from the reactor and enriched with aluminium trichloride in quantities equal to about 10% by weight with respect to the sludge.

In this stage two agitated reactors placed in series are used, so as to avoid the presence of unreacted chloroparaffins in the mixture leaving the alkylation stage, due to inevitable "short circuit" phenomena.

The reaction temperature is 60° C. and the volume of the two reactors allows a total stay time of about 1 hour in the alkylation stage.

The products leaving the alkylation stage are then decanted to separate the catalytic sludge, washed with 5 wt.% soda solution and then with water up to neutrality, and finally fractionated to separate the benzene, the unreacted paraffins and the alkylbenzenes. About 1,150 Kg/hour of paraffins which are intended for recycling and about 610 Kg/hour of alkylbenzenes are recovered. The heavy products are recovered at the foot of the distillation column for the alkylbenzenes in quantities equal to about 90 Kg/hour.

By proceeding under these conditions, a gradual increase in the chlorine content of the linear alkylbenzenes produced and in the content of secondary products of the recycled paraffins are noted.

When the chlorine content of the alkylbenzenes has reached a value of 200 ppm and their content of aromatic by-products has reached a value of 5% by weight, the unreacted paraffins recovered in the distillation stage in quantities equal to about 1,150 Kg/hours are no longer recycled directly to the chlorination stage but are fed to an absorption column filled with molecular sieves of the type 13 X described above, previously activated for 6 hours with nitrogen at 300°–350° C. and at atmospheric pressure.

The paraffins are passed through the column from the bottom towards the top. The absorption column, having a diameter of 32 cm and a height of 4 meters, contains 185 Kg of molecular sieves in the form of cylindrical extrusion of diameter 0.6 cm. During the whole operation a temperature of 120° C. and a pressure equal to atmospheric are maintained in the column; the average stay time of the paraffins on the molecular sieves is about 15 minutes.

The paraffins entering the absorption apparatus contain about 1% by weight of aromatic by-products and 700 ppm of organic chlorine.

In the paraffins leaving the absorption apparatus, the average content of aromatic by-products is reduced to 0.6% by weight and that of organic chlorine to 400 ppm.

The paraffins leaving the absorption apparatus are then directly recycled, together with 30% of fresh commercial paraffins, to the chlorination stage. There is thus obtained, in the linear alkylbenzenes produced by this continuous process, a lowering of the chlorine content down to about 50 ppm and of the content of aromatic products down to negligible levels.

The linear alkylbenzenes produced are, moreover, free from disagreeable odours and are of high quality.

After about 7 hours of continuous working the current of recycled paraffin to be purified is deviated, towards a second absorption column (B) containing the same type of molecular sieves and placed in parallel with the identical, first column (A) described above.

The exhausted molecular sieves of absorption column (A) are then subjected to a regeneration treatment.

This operation consists of a pre-treatment with a current of nitrogen at a temperature of 100° C. and at atmospheric pressure, for a period of time of two hours, to remove the paraffins remaining in the interstices between the molecular sieves. This is then followed by a stripping with nitrogen at a temperature of 300° C., at atmospheric pressure, for a period of time of about 2 hours, to remove the adsorbed impurities in the molecular sieves.

When, in continuation of the continuous process, the regenerated absorption column (A) is reinserted, in place of the column (B), in the purification cycle for the recycled paraffins, this has reaquired practically completely its initial absorbent capacity, both in the qualitative and in the quantitative sense, given that the impurities in the purified paraffins leaving it and in the final linear alkylbenzene products of the process are maintained constantly at the minimum values enumerated above. The process being carried out continuously, after eight complete cycles in which the absorption columns (A) and (B) are used alternately for the purification of the recycled paraffins and hence are from time to time regenerated, no appreciable variations in the results already given are noted.

EXAMPLE 2

The run of Example 1 was faithfully repeated, using, as the sole variant, a different method for the regeneration of the molecular sieves. The two columns were alternately subjected to the following three successive treatments:

(a) drying at 79° C., at atmospheric pressure, for two hours, with nitrogen;

(b) elution, still at 79° C., at atmospheric pressure, with benzene passed through the column from the bottom towards the top at a rate of 300 l/hour. After 2 hours the benzene issuing from the column was free from aromatic by-products and from organic chlorine, and its feed was stopped;

(c) stripping treatment with nitrogen at 180° C. and at atmospheric pressure, for 3 hours. In the course of the whole continuous operation results practically identical to those described in Example 1 were obtained constantly.

EXAMPLE 3

The run of Example 2 was faithfully repeated with the variant that, in the alternate regeneration of the molecular sieves, the treatment described at point (c) was abolished. Instead, the passage of the impure recycled paraffins was resumed directly.

The first fraction of the paraffins leaving the newly regenerated absorption column obviously contained a certain quantity of benzene, which was removed by distillation before this paraffin fraction was recycled, together with the remaining part of the purified recycled paraffins, to the chlorination stage.

In the course of the whole continuous operation, results practically identical to those obtained in Examples 1 and 2 were obtained continuously.

We claim:

1. In a process for the preparation of alkylbenzenes by partial chlorination of linear paraffins having from 9-15 carbon atoms per molecule, catalytic alkylation of benzene using the resulting mixture of chlorinated and unreacted paraffins, fractionation by distillation, after separation of the catalyst, of the alkylation products thus obtained and recycling of the unreacted paraffins recovered from the fractionation stage to the partial chlorination stage, the improvement which comprises submitting at least a part of the unreacted paraffins to be recycled to the partial chlorination stage, continuously or intermittently, to a purification treatment with molecular sieves selected from the group consisting of X and Y zeolites at a temperature ranging from ambient temperature to 200 degrees C and at a pressure ranging from 1-10 atmospheres to produce alkylbenzenes free from odor, having a chlorine content less than 100 ppm and wherein the treated unreacted paraffins have levels of all other impurities lower than levels detectable by flame gas-chromatography.

2. The process of claim 1, wherein said purification treatment is carried out at a temperature of from ambient temperature to 200° C., at a pressure of from 1 to 10 atmospheres and with an average residence time of the said unreacted paraffins on the molecular sieves of from 5 to 60 minutes.

3. The process of claim 1, wherein the molecular sieves are periodically regenerated by removing the substances absorbed in said molecular sieves by thermal stripping or by displacement by elution.

4. The process of claim 3, wherein said molecular sieves are regenerated when the amount of absorbed substances reaches a value of from 8 to 15% by weight with respect to the weight of said molecular sieves.

5. The process of claim 3, wherein the molecular sieves are subjected, before their periodic regeneration, to a pre-treatment of stripping with inert gas at a temperature of from ambient temperature to 150° C. and at a pressure of from 1 to 10 atmospheres, to recover the unreacted paraffins retained between the particles of said molecular sieves.

6. The process of claim 3, wherein the periodic regeneration is carried out by stripping with an inert gas at a temperature of from 250° to 400° C. and at a pressure of from 1 to 10 atmospheres.

7. The process of claim 3, wherein the periodic regeneration is carried out by elution with a light aromatic hydrocarbon solvent, at a temperature of from ambient temperature to the boiling point of the said solvent at the working pressure, said working pressure being from 1 to 10 atmospheres.

8. The process of claim 7, wherein said elution is followed by a stripping treatment with inert gas at a temperature of from 150° to 250° C. and at a pressure of from 1 to 10 atmospheres.

9. The process of claim 7, wherein said elution is followed by the direct resumption of the passage of the unreacted paraffins through the molecular sieves thus treated, the elution solvent present in the first fractions of unreacted paraffins submitted to purification after said direct resumption being removed by conventional methods before recycling to the partial chlorination stage.

10. The process of claim 7, wherein said elution solvent is benzene.

11. The process of claim 1, wherein said molecular sieves are of the type 13X.

12. The process of claim 1, wherein said molecular sieves have pore sizes varying between about 9 and 10 angstroms.

* * * * *